(12) United States Patent
Bartelme et al.

(10) Patent No.: US 9,017,337 B2
(45) Date of Patent: Apr. 28, 2015

(54) ACETABULAR ALIGNMENT GUIDE

(75) Inventors: Mike Bartelme, Fort Collins, CO (US);
Michal Slomczykowski, Buchrain (CH);
Ulrich Spaelter, München (DE)

(73) Assignee: DuPuy Orthopadie GmbH (DE)

( * ) Notice: Subject to any disclaimer, the term of this patent is extended or adjusted under 35 U.S.C. 154(b) by 1262 days.

(21) Appl. No.: 12/919,810

(22) PCT Filed: Feb. 26, 2009

(86) PCT No.: PCT/GB2009/000513
§ 371 (c)(1),
(2), (4) Date: Jan. 11, 2011

(87) PCT Pub. No.: WO2009/106813
PCT Pub. Date: Sep. 3, 2009

(65) Prior Publication Data
US 2011/0092979 A1 Apr. 21, 2011

(30) Foreign Application Priority Data
Feb. 28, 2008 (GB) .................................. 0803625.3

(51) Int. Cl.
*A61B 17/60* (2006.01)
*A61F 2/00* (2006.01)
*A61F 2/46* (2006.01)
*A61B 19/00* (2006.01)
*A61F 2/30* (2006.01)

(52) U.S. Cl.
CPC ....... *A61F 2/4609* (2013.01); *A61B 2019/5268* (2013.01); *A61B 2019/527* (2013.01); *A61F 2002/30545* (2013.01); *A61F 2002/30688* (2013.01); *A61F 2002/4632* (2013.01); *A61F 2250/001* (2013.01)

(58) Field of Classification Search
USPC .................. 606/53, 86 R, 87, 89, 91, 130, 99
See application file for complete search history.

(56) References Cited

U.S. PATENT DOCUMENTS

| 5,007,936 | A | | 4/1991 | Woolson | |
|---|---|---|---|---|---|
| 6,059,789 | A | * | 5/2000 | Dinger et al. | 606/96 |
| 6,395,005 | B1 | | 5/2002 | Lovell | |
| 6,589,281 | B2 | * | 7/2003 | Hyde, Jr. | 623/18.11 |
| 7,302,355 | B2 | * | 11/2007 | Jansen et al. | 702/95 |

(Continued)

FOREIGN PATENT DOCUMENTS

| EP | 1406203 A2 | 4/2004 |
|---|---|---|
| JP | 2005516662 A | 6/2005 |

(Continued)

OTHER PUBLICATIONS

GB Search Report GB0803625.3, dated May 20, 2008.
(Continued)

*Primary Examiner* — Anu Ramana

(57) ABSTRACT

An alignment guide for guiding the positioning of an acetabular cup implant includes a body having a first end and a second end. A flange extends from the first end and is adapted to rest on a labrum of an acetabulum. At least a first formation is provided at the second end which is adapted to engage with a transverse acetabular ligament of the acetabulum. A formation for accepting a trackable instrument is provided to allow a tracking system to determine the orientation of the guide.

19 Claims, 4 Drawing Sheets

(56) References Cited

U.S. PATENT DOCUMENTS

| | | |
|---|---|---|
| 8,206,405 B2 * | 6/2012 | Beverland et al. ............ 606/130 |
| 8,535,329 B2 * | 9/2013 | Sarin et al. .................... 606/102 |
| 2002/0077540 A1 | 6/2002 | Kienzle |
| 2003/0153829 A1 | 8/2003 | Sarin |
| 2004/0092944 A1 | 5/2004 | Penenberg |
| 2004/0117029 A1 | 6/2004 | Lewis |
| 2005/0021043 A1 | 1/2005 | Jansen |
| 2005/0065617 A1 | 3/2005 | Moctezuma de la Barrera |
| 2006/0094958 A1 | 5/2006 | Marquart |

FOREIGN PATENT DOCUMENTS

| | | |
|---|---|---|
| JP | 2007503289 A | 2/2007 |
| WO | WO 2004084740 A1 | 10/2004 |
| WO | WO 2006109022 A2 | 10/2006 |

OTHER PUBLICATIONS

PCT International Search Report and Written Opinion, PCT/GB2009/000513, dated Jul. 14, 2009.

* cited by examiner

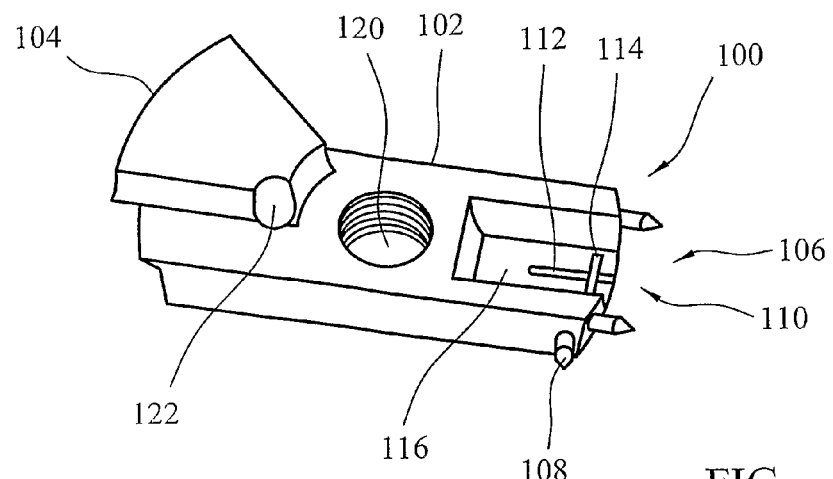
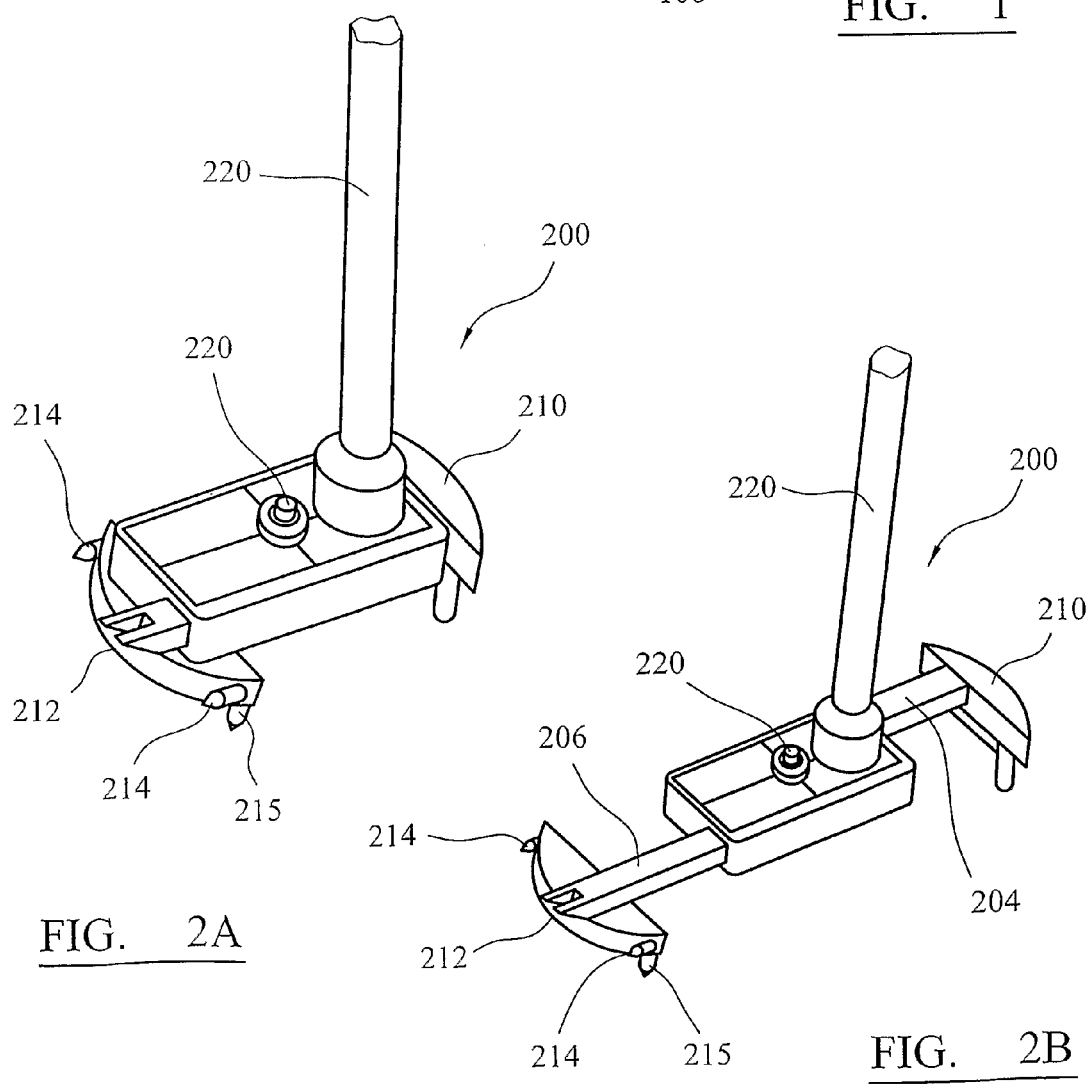
FIG. 1
FIG. 2A
FIG. 2B

FIG. 3A
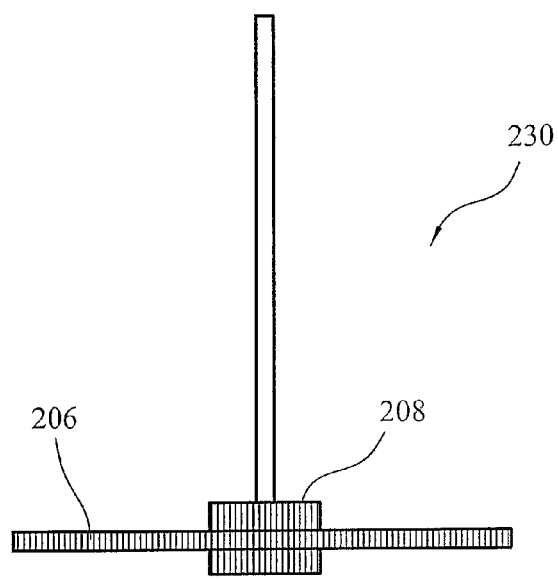
FIG. 3B
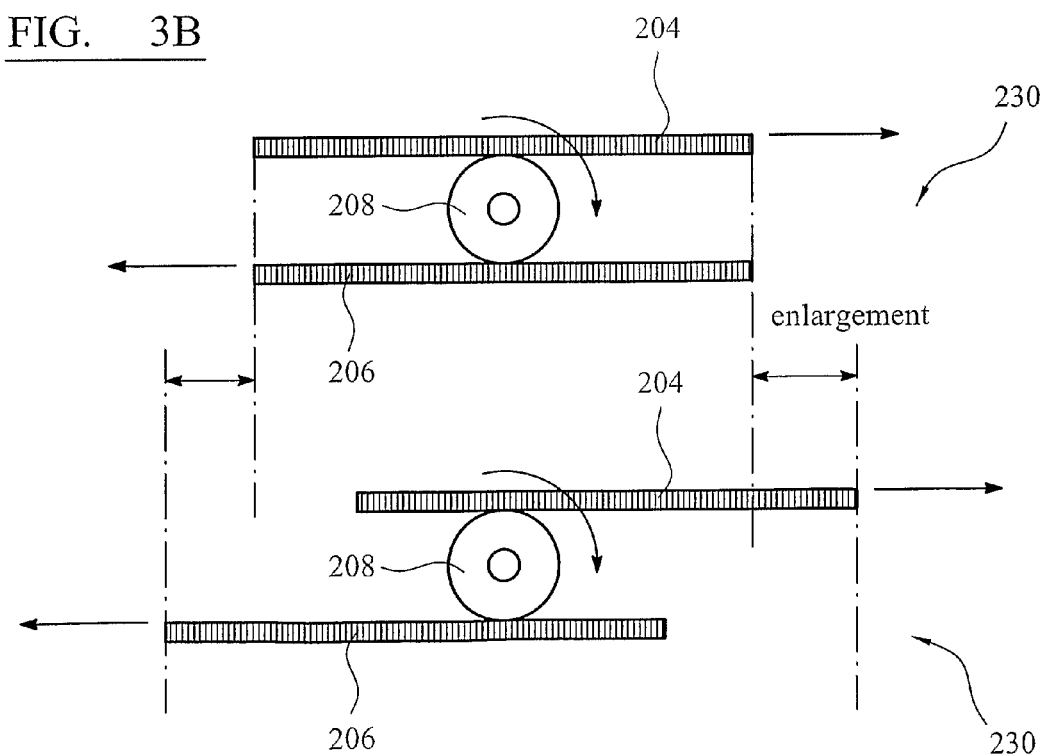
FIG. 3C

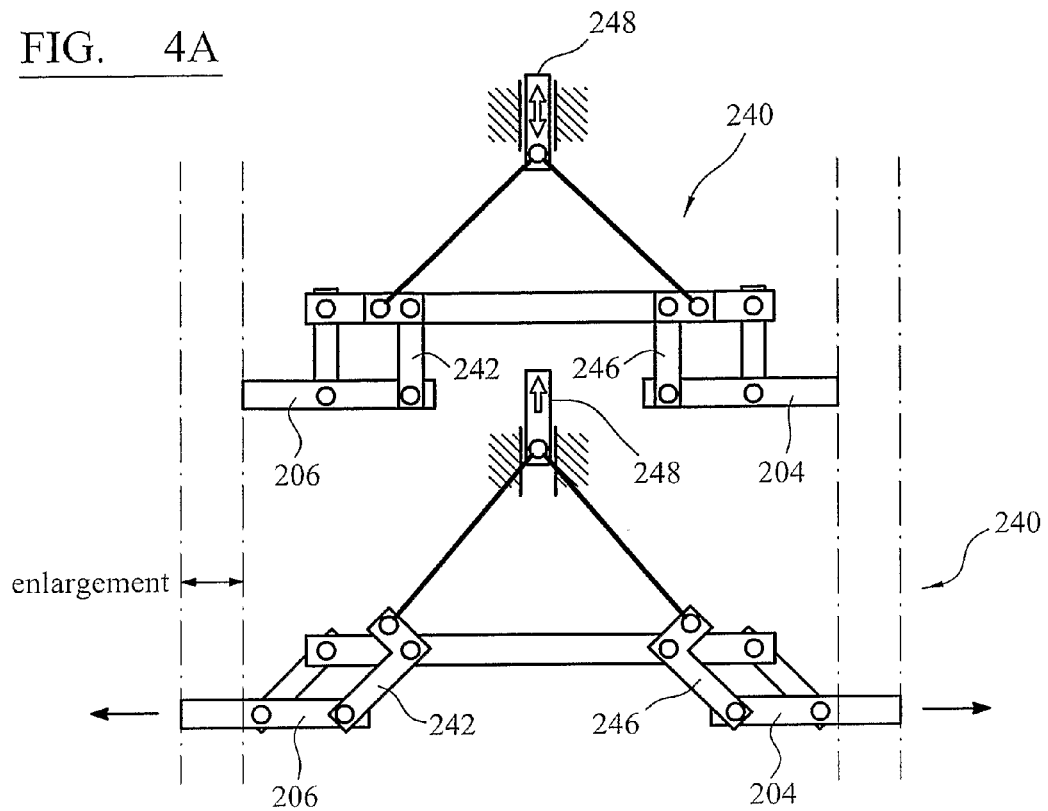
FIG. 4A
FIG. 4B
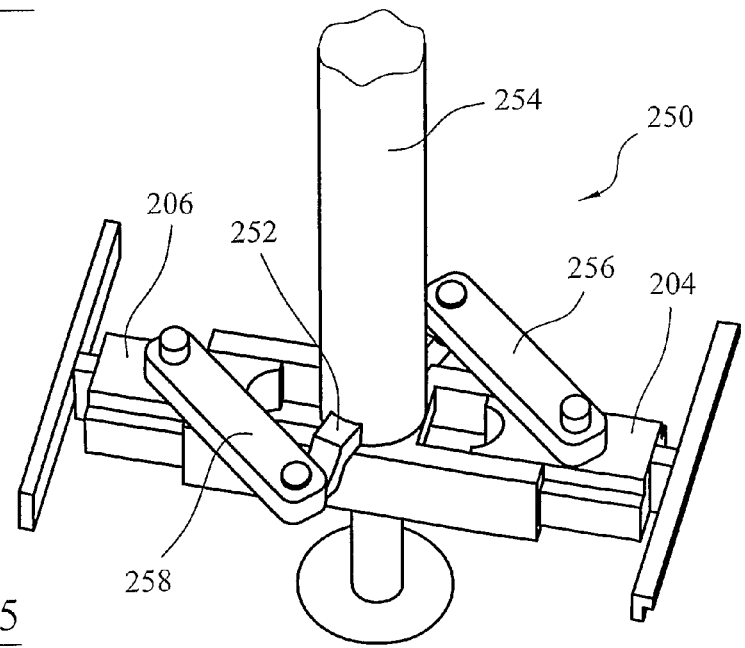
FIG. 5

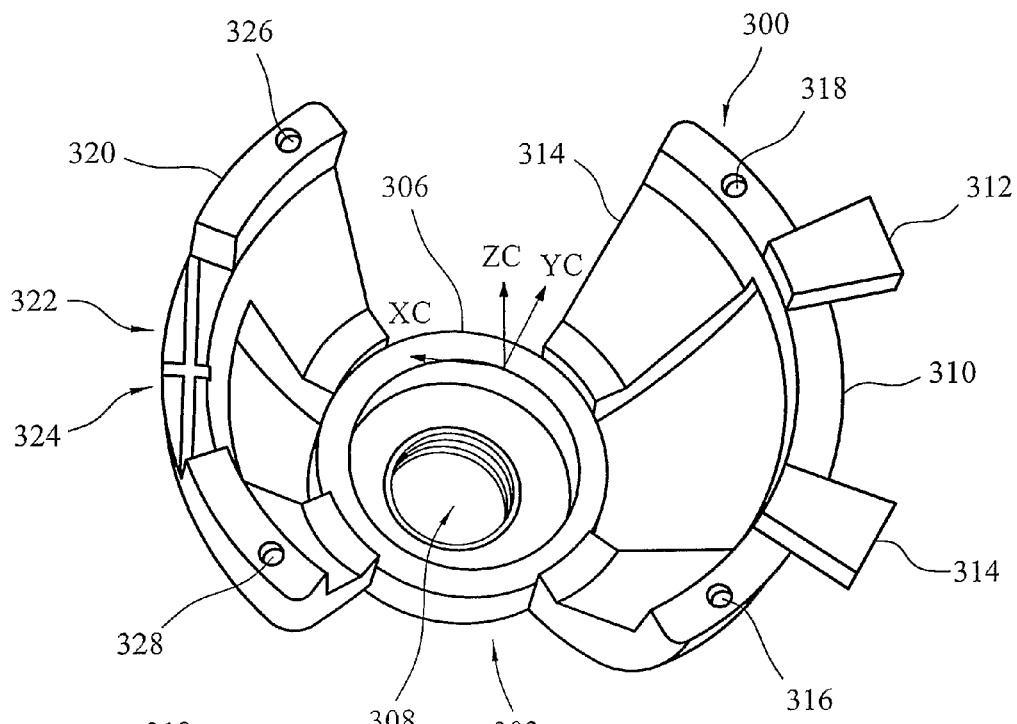
FIG. 6
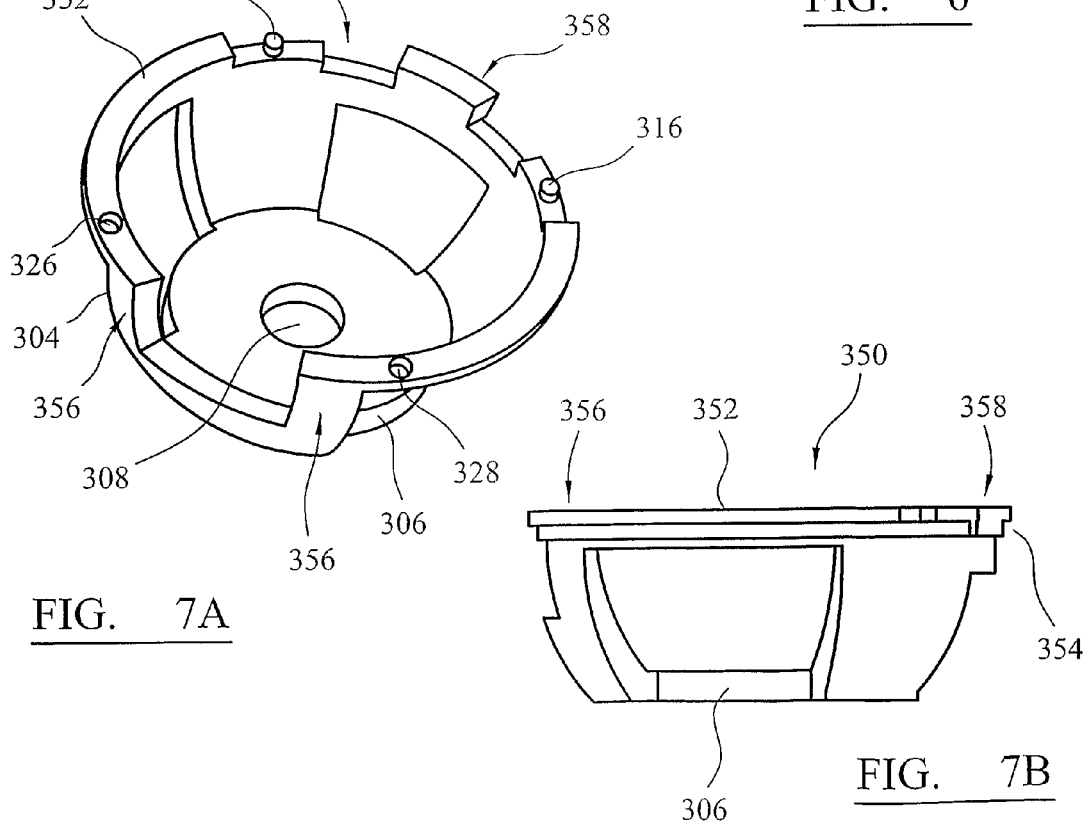
FIG. 7A
FIG. 7B

ACETABULAR ALIGNMENT GUIDE

CROSS REFERENCE TO RELATED PCT APPLICATION

This application is a National Stage 35 U.S.C. 371 of International Patent Application PCT/GB2009/000513, filed Feb. 26, 2009.

The present invention relates to an alignment guide, and in particular to an alignment guide for use in guiding the placement of an acetabular implant.

BACKGROUND OF THE INVENTION

International Patent application publication no. WO 2006/109022 describes a method for placing an acetabular implant, such as an acetabular cup, based on the position of a plane defined by the transverse acetabular ligament (TAL) and the labrum of the acetabulum. A computer assisted surgery (CAS) approach using a trackable pointer is described together with an instrument for a non-CAS approach. However, the CAS approach and instrument based approach may not be convenient where space is at a premium or where it is not easy to identify the TAL and labrum using a trackable pointer.

There is therefore a need for a simply way of guiding or planning the positioning of an acetabular cup implant.

BRIEF SUMMARY OF THE INVENTION

The present invention provides an alignment guide for guiding the positioning of an acetabular cup implant. The alignment guide can comprise a body having a first end and a second end. A flange can extend from the first end and can be adapted to rest on a labrum of an acetabulum in use. The second end can include a feature adapted to engage with a transverse acetabular ligament of the acetabulum in use. A formation for accepting a trackable instrument to allow a tracking system to determine the orientation of the guide can also be included.

The flange and feature allow the alignment guide to be positioned in an acetabulum generally parallel to the plane defined by the labrum and transverse acetabular ligament (TAL) and the formation allows a tracking system to determine the position of the alignment guide and therefrom the plane. That plane can then be used to navigate or plan the position of an acetabular trial or implant so as to restore the original joint.

The feature can be a feature or features which can partially or fully penetrate the TAL. The feature or features can extend around or along the second end to engage the TAL over a range of positions to help prevent the guide from pivoting about the feature or features. The features can be a plurality of prongs or spikes or similar. The feature can be an extended formation for presenting a gripping surface to the TAL. The combination of the feature or features and the flange can help ensure that the guide adopts a plane generally parallel to the plane defined by the TAL and labrum.

Preferably, the flange is a curved flange. This helps to support the guide on the curved labrum.

The curved flange can have a radius of curvature substantially the same as a radius of curvature of a labrum of an acetabulum. The radius can be in the range of from approximately 10 mm to 50 mm, more preferably approximately 15 mm to 40 mm and most preferably approximately 19 mm to 35 mm.

The first end of the body can be curved and/or the second end of the body can be curved. This helps to locate the alignment guide more accurately within the rounded opening of the acetabulum.

Preferably the first and second ends of the body are at opposed ends of the body.

The body can have a generally planar shape. The body can be generally rectangular in shape.

The body can have a generally cup like shape. The body can have an open structure. The body can be composed of a frame work of members.

The guide can have a plurality of prongs arranged at the second end for engaging the transverse acetabular ligament. Preferably at least two prongs are provided and they are space apart along the second end. The prongs can project within the plane of the body and/or along a longitudinal axis of the body. A second pair of prongs can be provided projecting in a downward direction from the body.

The formation can be located on the body of the guide. This makes it simpler to determine the position of the plane of the acetabulum as it is generally the same as the plane of the guide body when correctly positioned in the acetabulum.

The formation can be located at the centre of the body of the guide.

The formation can comprises an aperture configured to receive a trackable instrument to allow the inner surface of the acetabulum to be probed. This helps to allow the probe to access the bottom of the acetabulum.

The guide can further comprise a fitting for attaching a handle to the guide.

The guide can further comprise an adjustment mechanism operable to adjust the separation between the first and second ends of the guide. This allows the guide to be used with a variety of sizes of acetabuli.

The adjustment mechanism can include a pair of opposed racks engaging a common gear wheel rotatable to drive the pair of racks to adjust the separation between the first and second ends of the guide.

The guide can further comprise a recessed section or portion at or toward the second end to provide visibility of the transverse acetabular ligament in use.

The guide can further comprise an indicia or marking adjacent the second end of the guide providing an alignment reference for anteversion adjustment. Preferably the marking is in the form of a cross.

The guide can further comprise a marker trackable by a tracking system. This allows the position and/or orientation of the guide to be determined by a computer aided surgery system (CAS) to help determine the plane of the acetabulum when the guide is correctly positioned.

The feature can be a rim or a part or parts of a rim of the guide. The feature can be an outer edge or outer edges of the rim. The feature can be positioned generally diametrically opposite the flange.

A further aspect of the invention provides a kit of parts comprising any of the guide aspects of the invention and an instrument trackable by a tracking system, wherein the instrument is adapted to be engageable with the formation to allow the tracking system to determine the orientation of the guide.

A further aspect of the invention provides a method for guiding the placement of an acetabular cup implant in an acetabulum using an alignment guide, comprising: engaging a flange at a first end of the alignment guide with at least a part of the labrum of an acetabulum; engaging at least a first prong at a second end of the alignment guide with at least a part of the transverse acetabular ligament of the acetabulum; and determining the orientation of a plane defined by a body of the alignment guide while located in the acetabulum.

BRIEF DESCRIPTION OF THE DRAWINGS

Embodiments of the invention will now be described in detail, by way of example only, and with reference to the accompanying drawings, in which:

FIG. 1 shows a perspective views from above of a first alignment guide according to the invention;

FIGS. 2A and 2B show respective perspective views from above of a second alignment guide according to the invention in non-extended and extended states;

FIGS. 3A and 3B show respective side and plan views of a first size adjustment mechanism for the second alignment guide shown in FIGS. 2A and 2B;

FIG. 3C shows a plan view of the second alignment guide shown in FIGS. 2A and 2B, illustrating the alignment guide in an extended state.

FIGS. 4A and 4B show respective side views of a second size adjustment mechanism for the second alignment guide;

FIG. 5 shows a perspective view of a third size adjustment mechanism for the second alignment guide;

FIG. 6 shows a perspective view from above of a third alignment guide according to the invention; and FIGS. 7A and &B show respective perspective and side views of a fourth alignment guide according to the invention.

Similar items in difference Figures share common reference signs unless indicated otherwise.

DETAILED DESCRIPTION OF THE INVENTION

FIG. 1 shows a perspective view of a first embodiment of an acetabular alignment guide 100 according to the invention. The alignment guide 100, has a body 102 with a generally plate-like shape. A first end of the body and a second end of the body are each curved and form a part of the circumference of a circle. A curved flange, rim or lip 104 extends from the first end of the body. A first pair of prongs 106 extend from the second end of the body and in a direction generally parallel to the longitudinal axis of the body. A second set of prongs, of which the tip of a one of them can be seen in FIG. 1, extend downwardly from an underside of the body and are located toward either side of the body 102. A recessed portion 110 is provided in the body toward the second end. A first 112 and a second 114 marking are provided on a floor 116 of the recess. The first 112 marking extends in a direction generally parallel to the longitudinal axis of the body and is located at the middle of the body. The second marking 114 extends in a direction generally perpendicular to that of the first marking and forms a part of a chord of the circle defined by the curved ends of the alignment guide (i.e. is generally parallel to a tangent to the curve of the second end).

A threaded aperture 120 is provided at the centre of the body for receiving a threaded end of an insertion instrument in use. A blind hole 122 is also provided as a registration formation for receiving the tip of a navigated pointer instrument as will be described in greater detail below. The hole 122 lies on the middle of the body. In an alternate embodiment, the hole 122 is located at the centre of the body, in place of threaded aperture 120, and the threaded aperture is off set toward the first end of the body.

The flange 104 is shaped, sized and otherwise configured to rest on the labrum of an acetabulum in use. The prongs 106 are shaped, sized and otherwise configured to penetrate the transverse acetabular ligament (TAL) of an acetabulum in use. At least two prongs are preferred to securely anchor the alignment guide and prevent it wobbling in use.

The alignment guide 100 can be made of a suitable surgical standard metal or alloy, such as stainless steel or titanium, or of a suitable plastics, such as PEEK, or composite materials. The alignment guide can be provided in a variety of sizes to be used with acetabuli having diameters ranging from approximately 38 mm to 70 mm.

The method of use of the first embodiment will now be described. It will be appreciated that the method of use is generally similar for all the embodiments of the alignment guide described herein. The alignment guide is used with a computer assisted surgery (CAS) system which includes a tracking technology allowing the positions of various instruments, implants and devices used by the surgeon to be tracked.

Initially the surgeon obtains visual access to the acetabulum and dislocates the head of the femur. The surgeon then identifies the TAL and the remnants of the labrum. As described in WO 2006/109022, the disclosure of which is incorporated herein by reference for all purposes, it has been found that the plane defined by the TAL and labrum can be used to align an acetabular cup implant to help restore the hip joint. The alignment guide 100 is used to help identify more accurately that plane. The alignment guide is positioned in the mouth of the acetabulum, with the prongs engaging the TAL and the flange 104 resting on the labrum. The alignment guide can be manoeuvered into position using an inserter handler attached to the guide by threaded aperture 120. The cross formation of the markings 112, 114 provide a precisely defined alignment reference to help adjust the anteversion direction of the alignment guide. The alignment guide rim, which contacts the TAL, should be aligned in parallel with the TAL and the 'tangential' marking helps provide a visual cue using which the alignment guide can be aligned with the TAL. Further, the alignment guide should be correctly centred with respect to the TAL and the markings are useful in centring the alignment guide. The marking does not need to be in a cross shape and other combinations of markings can be used to help in aligning and/or centring the guide. The recessed portion 110 provides improved visibility of the TAL which would otherwise be covered.

Then, the surgeon uses a navigated pointer, or other instrument trackable by the CAS system, to allow the CAS system to determine the position of the plane defined by the plane of the body of the alignment guide. This can be achieved in a number of ways. In a first approach, the surgeon identifies at least three points on the surface of the alignment guide which the CAS system captures and from which the CAS system can then determine the plane of the alignment guide and its position. In another embodiment, the hole 122 is not blind but passes through the alignment guide and the end of the pointer is passed through the hole so that the axis of the pointer defines a direction perpendicular to the plane of the alignment guide body and so the direction of the plane of the alignment guide can be determined.

In the embodiment in which the hole 122 is located centrally, the pointer passes through the hole and brought to rest at the centre of the bottom of the acetabulum and again the direction of the axis of the probe is perpendicular to the plane of the alignment guide and so the direction of the plane of the alignment guide can be determined from the direction of the longitudinal axis of the trackable probe. A number of approaches can be used to determine the depth of the acetabulum and thereby the size of implant required (assuming the acetabulum to be approximately hemispherical). In a first approach, a separate registration point on the plate surface and at its centre is captured using a marked probe and the depth of the acetabulum can be determined from the separation of that point and the captured point at the centre of the bottom of the acetabulum. Obviously the order in which the points is collected is immaterial. Alternatively, the position of the point on the surface of the alignment guide can be captured at the same time as the point at the centre of the bottom of the acetabulum, using another marked pointer or using a marker which is attached to the alignment guide.

Hence, the CAS system has now captured the direction of the plane defined by the TAL and labrum and that direction can be used subsequently during navigated placement of the acetabular trail and/or acetabular cup implant during the remainder of the surgical procedure.

FIGS. 2A and 2B show perspective views of a second embodiment of the alignment guide 200 of the invention. The alignment guide includes an adjustment mechanism allowing its size to be changed so that it can be used with different sized acetabuli. The alignment guide again includes a generally plate like shaped body 202, having a first end and a second end. The body 202 houses the size adjustment mechanism which includes a pair of arms 204, 206 bearing teeth and which are driven by a central toothed wheel 208 as illustrated in FIGS. 3A-3C, which show the size adjustment mechanism 230 in greater detail. First arm 204 bears a curved rim or flange 210 at a first end of the guide for resting on a labrum. Second arm 206 bears a curved member 212 at a second end of the alignment guide and having a first pair of prongs 214 extending longitudinally from an end face of member 212 and a second pair of prongs (only one of which 215 can be seen) extending downwardly from an under side face of curved member 212. An upper face of curved member 212 bears markings similar to those of the first embodiment.

FIGS. 2A and 2B also show part 220 of an insertion instrument attached to the alignment guide by a threaded hole. A centrally located through hole 220 is also provided to accept a trackable pointer there through in use, as described above.

Use of the alignment guide 200 is similar to that for alignment guide 100, except the size of the alignment guide 200 can be adjusted to match the size of the acetabulum. As illustrated in FIG. 2A, which corresponds to FIG. 3B, the alignment guide has a non-extended mode in which it has its smallest size with the two end portions adjacent the body. By rotating the central toothed wheel 208, the arms 204, 206 are driven, illustrated by FIG. 3C, and the end portions moved away from the body, so that the guide adopts a second extended state, as illustrated in FIG. 2B. It will be appreciated that other adjustment mechanisms can also be used instead of the adjustment mechanism 230 illustrated in FIGS. 3A-3C.

FIGS. 4A and 4B show side views of a second size adjustment mechanism 240 which can be used in the alignment guide of the invention. FIG. 4A shows the mechanism in a non-extended state and FIG. 4B the mechanism in an extended state. The adjustment mechanism includes a multi-arm parallelogram linkage, in which the arms 204, 206 of the guide can be driven outward and inward by actuating lever arms 242, 242 by pulling and pushing on drive member 248. It is also possible to use a scissors-linkage based adjustment mechanism.

FIG. 5 shows a perspective view of a third size adjustment mechanism 250 which can be used in the alignment guide of the invention. A central shaft 252 bears a crank 254 having members 256, 258 pivotally attached to the ends thereof and also pivotally attached to respective arms 204, 206. Hence, by rotating shaft 254, arms 204, 206 can be driven in and out of the main body housing to adjust the size of the alignment guide.

FIG. 6 shows a third embodiment of an alignment guide 300 according to the invention. The body 302 of the alignment guide is generally cup shaped and is formed from an open framework 304 or cage extending from a central hub 306 with a central threaded aperture 308 therein for receiving a matching thread of an end of an insertion instrument. A first end of the body includes a first curved member 310 being a portion of a circle and bearing two flanges or rim parts 312, 314 extending therefrom. Two dimples 316, 318 are provided on the curved member for receiving the tip of a navigated pointer to register the plane of the alignment guide as described above. A second end of the body includes a second curved member 320 being a portion of the same circle as the first curved member and including a recessed portion 322 bearing crossed marks 324. A further two dimples 326, 328 are provided similarly to dimples 316, 318. It will be appreciated that in this embodiment the curved parts 310, 320 of the body define the plane of the acetabulum with which the acetabular cup should be aligned and that the positions of at least three of dimples 316, 318, 326, 328 can be captured to determine that plane.

The outer edges of curved portion 320, generally diametrically opposed to the flanges 312, 314, provide the feature or engagement formation for engaging with the TAL in use. The plate like instruments described above risk being tilted about their longitudinal axis and therefore prongs are preferred for those embodiments to provide the engagement formations. However, as the embodiments described with reference to FIG. 6 (and FIG. 7 below) are generally symmetric, share a large contact area with the acetabulum and are stemmed into the acetabulum, the risk of them wobbling is greatly reduced. Further, fine tuning of the position of the alignment guide after insertion is possible by omitting prongs.

FIG. 7 shows a further embodiment of an alignment guide 350, similar to that shown in FIG. 6. The alignment guide shown in FIG. 6 can only be used with a single acetabulum size. The alignment guide 350 has a rim 352 with a plurality of steps 354 in it. Each steps acts as a flange which can engage the labrum for different diameter acetabuli. That is the higher steps can be used as the flange for a large diameter acetabulum and the lower steps can be used as the flange for a smaller diameter acetabulum. Similarly to the embodiment shown in FIG. 6, the outer edge parts of the rim 356 generally diametrically opposite to the labrum engaging portion 358 of the rim provide a TAL engagement formation or feature of the alignment guide.

It will be appreciated that various modifications and changes can be made to the specific embodiments described herein and that features of one embodiment can be used with other embodiments.

The invention claimed is:

1. An alignment guide for guiding the positioning of an acetabular cup implant, comprising:
    a body having a first end and a second end;
    a flange extending from the first end and adapted to rest on a labrum of an acetabulum;
    at least one prong at the second end adapted to engage with a transverse acetabular ligament of the acetabulum; and
    a formation for accepting a trackable instrument to allow a tracking system to determine the orientation of the guide; wherein the flange is a curved flange.

2. The guide of claim 1, wherein the curved flange has a radius of curvature substantially the same as a radius of curvature of a labrum of an acetabulum.

3. The guide of claim 1, wherein the first end of the body is curved.

4. The guide of claim 3, wherein the second end of the body is curved.

5. The guide of claim 1, wherein the first and second ends of the body are at opposed ends of the body.

6. The guide of claim 1, wherein the body has a generally planar shape.

7. The guide of claim 1, wherein the body has a generally cup like shape.

8. The guide of claim 1, wherein the at least one prong is a plurality of prongs arranged at the second end for penetrating the transverse acetabular ligament.

9. The guide of claim 8, wherein the formation is located at the centre of the body of the guide.

10. The guide of claim 1, wherein the formation is located on the body of the guide.

11. The guide of claim 10, wherein the formation comprises an aperture configured to receive a trackable instrument to allow the inner surface of the acetabulum to be probed.

12. The guide of claim 1, further comprising a fitting for attaching a handle to the guide.

13. The guide of claim 1, further comprising an adjustment mechanism operable to adjust the separation between the first and second ends of the guide.

14. The guide of claim 13, wherein the adjustment mechanism includes a pair of opposed racks engaging a common gear wheel rotatable to drive the pair of racks to adjust the separation between the first and second ends of the guide.

15. The guide of claim 1, and further comprising a recessed section at the second end to provide visibility of the transverse acetabular ligament in use.

16. The guide of claim 1, and further comprising a marking adjacent the second end of the guide providing an alignment reference for anteversion adjustment.

17. The guide of claim 1 and further comprising a marker trackable by a tracking system.

18. A kit of parts comprising the guide of claim 1 and an instrument trackable by a tracking system, wherein the instrument is adapted to be engageable with the formation to allow the tracking system to determine the orientation of the guide.

19. A method for guiding the placement of an acetabular cup implant in an acetabulum using an alignment guide, comprising:

engaging a flange at a first end of the alignment guide with at least a part of the labrum of an acetabulum;

engaging at least one prong at a second end of the alignment guide with at least a part of the transverse acetabular ligament of the acetabulum; and determining the orientation of a plane defined by a body of the alignment guide while located in the acetabulum.

\* \* \* \* \*